United States Patent

Ishihara et al.

Patent Number: 5,705,527
Date of Patent: Jan. 6, 1998

[54] AMINO ACID DERIVATIVES

[75] Inventors: Sadao Ishihara; Fujio Saito; Takao Yoshioka; Hiroyuki Koike; Shigeki Miyake; Hiroshi Mizuno, all of Tokyo, Japan

[73] Assignee: Sankyo Company, Limited, Tokyo, Japan

[21] Appl. No.: 426,017

[22] Filed: Apr. 20, 1995

Related U.S. Application Data

[63] Continuation of Ser. No. 170,174, filed as PCT/JP92/00823, Jun. 30, 1992, published as WO93/01163, Jan. 21, 1993, abandoned.

[30] Foreign Application Priority Data

Jul. 4, 1991 [JP] Japan ................................. 3-164585

[51] Int. Cl.⁶ ................ A61K 31/335; A61K 31/04; C07D 317/34; C07D 203/02
[52] U.S. Cl. ................ 514/467; 514/343; 514/365; 514/399; 514/400; 514/419; 514/459; 514/509; 546/279.4; 548/204; 548/205; 548/338.1; 548/340.1; 548/496; 548/507; 549/229; 549/425; 549/426; 549/427; 558/483
[58] Field of Search ............ 546/279.4; 548/204, 548/205, 388.1, 340.1, 496, 507; 549/229, 425, 426, 427; 558/483; 514/343, 365, 399, 400, 419, 459, 467, 509

[56] References Cited

U.S. PATENT DOCUMENTS

| | | | |
|---|---|---|---|
| 5,037,849 | 8/1991 | Simon et al. | 514/509 |
| 5,284,872 | 2/1994 | Sandrock et al. | 514/509 |

*Primary Examiner*—Ba K. Trinh
*Attorney, Agent, or Firm*—Frishauf, Holtz, Goodman, Langer & Chick, P.C.

[57] ABSTRACT

An amino acid compound of the formula: $R^1NH-CH(R^2)-COHN-A-ONO_2$, wherein $R^1$ represents a hydrogen atom, a $C_1-C_7$ alkanoyl group, a $C_1-C_6$ alkoxycarbonyl group, a $C_6-C_{10}$ arylcarbonyl group, a $C_7-C_{13}$ aralkylcarbonyl group, a $C_7-C_{13}$ aralkyloxycarbonyl group or a 5- or 6-membered aromatic heterocyclic carbonyl group; $R^2$ represents a substituted $C_1-C_6$ alkyl group; and A represents a $C_2-C_5$ alkylene group; and pharmacologically acceptable salts thereof. The amino acid compound has an excellent vasodilator action for collateral vessels and is useful for treating angina pectoris.

19 Claims, No Drawings

AMINO ACID DERIVATIVES

This application is a Continuation of application Ser. No. 08/170,174, filed Dec. 17, 1993, now abandoned which is the United States national phase 371 application of International Application No. PCT/JP92/00823 filed Jun. 30, 1992.

FIELD OF THE INVENTION

The present invention relates to an amino acid derivative and pharmacologically acceptable salts thereof having an excellent vasodilator action for collateral vessels and an anti-anginal action.

BACKGROUND OF THE INVENTION

Nitroglycerine has so far been most frequently used clinically as a therapeutic drug for cardiovascular diseases, particularly angina pectoris. However, nitroglycerine is susceptible to undergo a first-pass effect and has a short duration of action, disadvantageously. In addition, headaches, dizziness, and tachycardia due to the depression of blood pressure are brought about as side effects. There have been desired antianginal drugs for clinical treatment which undergo no first-pass effect and have excellent duration of action.

Meanwhile, as a amino acid derivative having antianginal action, alanine derivatives, for example, are known (e.g. Japan Kokai No. Hei-2-169558).

SUMMARY OF THE INVENTION

The present inventors have prepared for long years a series of amino acid derivatives and examined their pharmacological actions. As the result, they found that specific amino acid derivatives have an excellent duration of vasodilator action for collateral vessels with less side effects as well as less drug tolerance and are useful as therapeutic drugs, and they accomplished the present invention.

The amino acid derivative of the present invention has the general formula:

$$R^1NH—CH(R^2)—CONH—A—ONO_2 \qquad (I).$$

In the above formula, $R^1$ represents a hydrogen atom, a $C_1$–$C_7$ alkanoyl group, a $C_1$–$C_6$ alkoxycarbonyl group, a $C_6$–$C_{10}$ arylcarbonyl group, a $C_7$–$C_{13}$ aralkylcarbonyl group, a $C_7$–$C_{13}$ aralkyloxycarbonyl group or a 5- or 6-membered aromatic heterocyclic carbonyl group containing 1 to 3 nitrogen atoms, oxygen atoms or sulfur atoms;

$R^2$ represents a $C_1$–$C_6$ alkyl group having a substituent (said substituent is a $C_6$–$C_{10}$ aryl group, a mercapto group, a $C_1$–$C_6$ alkylthio group, a $C_1$–$C_7$ alkanoylthio group, a $C_1$–$C_6$ alkoxycarbonylthio group, (5-methyl- or 5-phenyl-2-oxo-1,3-dioxolen-4-yl)methoxycarbonylthio group, a $C_6$–$C_{10}$ arylcarbonylthio group, a $C_7$–$C_{13}$ aralkylcarbonylthio group, a 5- or 6-membered aromatic heterocyclic carbonylthio group having 1 to 3 nitrogen atoms, oxygen atoms or sulfur atoms, a hydroxy group, a $C_1$–$C_6$ alkoxy group, a $C_1$–$C_7$ alkanoyloxy group, a $C_1$–$C_6$ alkoxycarbonyloxy group, a $C_6$–$C_{10}$ arylcarbonyloxy group, a $C_7$–$C_{13}$ aralkylcarbonyloxy group, a 5- or 6-membered aromatic heterocyclic carbonyloxy group having 1 to 3 nitrogen atoms, oxygen atoms or sulfur atoms, an amino group, a mono- or di-$C_1$–$C_6$ alkylamino group, a $C_1$–$C_7$ alkanoylamino group, a $C_1$–$C_6$ alkoxycarbonylamino group, a $C_6$–$C_{10}$ arylcarbonylamino group, a $C_7$–$C_{13}$ aralkylcarbonylamino group, a 5- or 6-membered aromatic heterocyclic carbonylamino group having 1 to 3 nitrogen atoms, oxygen atoms or sulfur atoms, or 5- or 6-membered aromatic heterocyclic group having 1 to 3 nitrogen atoms, oxygen atoms or sulfur atoms.) or a $C_6$–$C_{10}$ aryl group; and A represents a $C_2$–$C_5$ alkylene group.

DETAILED DESCRIPTION OF THE INVENTION

The alkyl moiety of the $C_1$–$C_6$ alkoxycarbonyl group of $R^1$, $C_1$–$C_6$ alkyl group having a substituent of $R^2$ or the $C_1$–$C_6$ alkylthio group, $C_1$–$C_6$ alkoxycarbonylthio group, $C_1$–$C_6$ alkoxy group, $C_1$–$C_6$ alkoxycarbonyloxy group, $C_1$–$C_6$ alkylamino group, $C_1$–$C_6$ alkoxycarbonylamino group, etc., included in $R^2$ may be, for example, a methyl, ethyl, propyl, isopropyl, butyl, sec-butyl, t-butyl, isobutyl, pentyl or hexyl group, preferably a $C_1$–$C_4$ alkyl group, more preferably a methyl or ethyl group.

The $C_1$–$C_7$ alkanoyl group of $R^1$ or the $C_1$–$C_7$ alkanoyl moiety of the $C_1$–$C_7$ alkanoylthio group, $C_1$–$C_7$ alkanoyloxy group, $C_1$–$C_7$ alkanoylamino group, etc., included in $R^2$ may be, for example, a formyl, acetyl, propionyl, butyryl, isobutyryl, pivaloyl, valeryl, isovaleryl, hexanoyl or heptanoyl group, preferably a $C_2$–$C_5$ alkanoyl group, more preferably an acetyl, propionyl or isobutyryl group.

The $C_6$–$C_{10}$ aryl group of $R^2$, the $C_6$–$C_{10}$ aryl group included in $R^2$ or the $C_6$–$C_{10}$ aryl moiety of the $C_6$–$C_{10}$ arylcarbonyl group of $R^1$, and that of the $C_6$–$C_{10}$ arylcarbonylthio group, the $C_6$–$C_{10}$ arylcarbonyloxy group, the $C_6$–$C_{10}$ arylcarbonylamino group, etc., included in $R^2$ may be, for example, a phenyl or naphthyl group, preferably a phenyl group. Further, the $C_6$–$C_{10}$ aryl moiety may have substituents on the ring, and they include, for example, a $C_1$–$C_6$ alkyl group, a $C_1$–$C_6$ alkoxy group, a halogen atom (e.g. fluorine, chlorine, bromine or iodine atoms), a hydroxy group and an amino group, preferably a methyl, ethyl, methoxy, ethoxy, fluorine, chlorine, hydroxy or amino group for the substituents for the $C_6$–$C_{10}$ aryl group included in $R^2$, particularly preferably a hydroxy group; and methyl, ethyl, methoxy, ethoxy, fluorine and chlorine for other substituents.

The $C_7$–$C_{13}$ aralkyl moiety of the $C_7$–$C_{13}$ aralkylcarbonyl group of $R^1$, the $C_7$–$C_{13}$ aralkyloxycarbonyl group of $R^1$ or of the $C_7$–$C_{13}$ aralkylcarbonylthio group, etc., $C_7$–$C_{13}$ aralkylcarbonyloxy group, $C_7$–$C_{13}$ aralkylcarbonylamino group included in $R^2$ may be, for example, a benzyl, phenethyl, 1-phenethylethyl, 2-phenylpropyl, 3-phenylpropyl, diphenylmethyl, 1-naphthylmethyl or 2-naphthylmethyl group, preferably a ($C_1$–$C_4$ alkyl)phenyl group, more preferably a benzyl or phenethyl group. Further, $C_7$–$C_{13}$ aralkyl moiety may have substituents on the ring, and they include those as described for the above arylcarbonyl group.

The 5- or 6-membered aromatic heterocyclic group containing 1 to 3 nitrogen atoms, oxygen atoms or sulfur atoms included in $R^2$; or the 5- or 6-membered aromatic heterocyclic moiety of the 5- or 6-membered aromatic heterocyclic carbonyl group containing 1 to 3 nitrogen atoms, oxygen atoms or sulfur atoms of $R^1$ the 5- and 6-membered aromatic heterocyclic carbonylthio group, 5- or 6-membered aromatic heterocyclic carbonyloxy group, 5- or 6-membered aromatic heterocyclic carbonylamino group, etc., included in $R^2$ may be condensed with a phenyl ring, and may be, for example, a furyl, thienyl, pyrrolyl, oxazolyl, isoxazolyl, thiazolyl, isothiazolylo imidazolyl, triazolyl, pyrazolyl, pyridyl, pyridadinyl, pyrimidinyl, indolyl, quinolyl or quinazolinyl group, preferably a 5- or 6-membered aromatic heterocyclic group containing 1 or 2 nitrogen atoms, oxygen atoms or sulfur atoms, more preferably a furyl, thienyl, oxazolyl, isoxazolyl, thiazolyl, isothiazolyl, pyridyl or indolyl group. With respect to the 5- or 6-membered aromatic heterocyclic group included in $R^2$ far more preferably includes a furyl, imidazolyl, thienyl, pyridyl, thiazolyl or indolyl group, particularly preferably a pyridyl group. Other 5- or 6-membered aromatic heterocyclic groups far more preferably include a 5- or 6-membered aromatic heterocyclic group containing 1 nitrogen atom, oxygen atom or sulfur atom, and particularly preferably furyl, thienyl and pyridyl groups. The 5- and 6-membered aromatic heterocyclic moiety may have substituents on the ring, and they may be, for example, a $C_1$–$C_6$ alkyl group or a $C_1$–$C_6$ alkoxy group, preferably a methyl, ethyl, methoxy or ethoxy group.

The $C_2$–$C_5$ alkylene group of A may be, for example, ethylene, propylene, trimethylene, tetramethylene or pentamethylene, preferably a $C_2$–$C_3$ alkylene group, more preferably an ethylene group.

In the compound represented by the general formula (I), the carbon atom to which $R^2$ is attached can be an asymmetric carbon atom, and optical isomers based on such carbon atom are present, and it is preferably an L-compound. In addition, these isomers and mixtures thereof are included in the present invention.

Further, the compound (I) can be converted to pharmacologically acceptable salts. When the compound (I) has basic groups such as amino, alkylamino, etc., the salts may be exemplified by those with inorganic acids such as hydrochloric acid, sulfuric acid, nitric acid and phosphoric acid, and those with organic acids such as acetic acid, propionic acid, lactic acid, malonic acid, succinic acid, maleic acid, fumaric acid, methanesulfonic acid and p-toluenesulfonic acid. When the compound (I) has acidic groups such as phenolic hydroxy, etc., the salts can be exemplified by those with alkali metals such as lithium, sodium and potassium.

The compound having the above general formula (I) preferably includes;

1) a compound wherein $R^1$ is a hydrogen atom, a $C_1$–$C_5$ alkanoyl group, a $C_1$–$C_4$ alkoxycarbonyl group, a $C_7$ aralkyloxycarbonyl group or a 5- or 6-membered aromatic heterocyclic carbonyl group containing 1 nitrogen atom, oxygen atom or sulfur atom;

2) a compound wherein $R^2$ is a $C_1$–$C_4$ alkyl group having a substituent (said substituent is a $C_6$ aryl group, a naphthyl group, a mercapto group, a $C_1$–$C_4$ alkylthio group, a $C_1$–$C_5$ alkanoylthio group, a $C_1$–$C_4$ alkoxycarbonylthio group, (5-methyl- or 5-Phenyl-2-oxo-1,3-dioxolen-4-yl)methoxycarbonylthio group, a $C_6$–$C_{10}$ arylcarbonylthio group, a $C_7$–$C_{10}$ aralkylcarbonylthio group, a 5- or 6-membered aromatic heterocyclic carbonylthio group containing 1 nitrogen atom, oxygen atom or sulfur atom, a hydroxy group, a $C_1$–$C_4$ alkykoxy group, a $C_1$–$C_5$ alkanoyloxy group, a $C_1$–$C_4$ alkoxycarbonyloxy group, a $C_6$–$C_{10}$ arylcarbonyloxy group, a 5- or 6-membered aromatic heterocyclic carbonyloxy group containing 1 nitrogen atom, oxygen atom or sulfur atom, an amino group, a $C_1$–$C_5$ alkanoylamino group, a $C_1$–$C_4$ alkoxycarbonylamino group, a $C_6$–$C_{10}$ arylcarbonylamino group, a 5- or 6-membered aromatic heterocyclic carbonylamino group containing 1 nitrogen atom, oxygen atom or sulfur atom or a 5- or 6-membered cyclic aromatic heterocyclic group containing 1 or 2 nitrogen atoms, oxygen atoms or sulfur atoms.) or a $C_6$ aryl group; and 3) a compound wherein A is a $C_2$–$C_3$ alkylene group; more preferably 4) a compound wherein $R^1$ is a hydrogen atom, a $C_1$–$C_5$ alkanoyl group, a $C_1$–$C_4$ alkoxycarbonyl group, a benzyloxycarbonyl group, a furylcarbonyl group, a thienylcarbonyl group, a nicotinoyl group or an isonicotinoyl group;

5) a compound wherein $R^2$ is a $C_1$–$C_4$ alkyl group having a substituent (said substituent is a phenyl group, a 4-hydroxyphenyl group, a mercapto group, a $C_1$–$C_2$ alkylthio group, a $C_1$–$C_5$ alkanoylthio group, a $C_1$–$C_4$ alkoxycarbonylthio group, a (5-methyl- or 5-phenyl-2-oxo-1,3-dioxolen-4-yl)methoxycarbonylthio group, a $C_6$–$C_{10}$ arylcarbonylthio group, a $C_7$ aralkylcarbonylthio group, a 5- or 6-membered aromatic heterocyclic carbonylthio group containing 1 nitrogen atom, oxygen atom or sulfur atom, a hydroxy group, a $C_1$–$C_5$ alkanoyloxy group, a $C_1$–$C_4$ alkoxycarbonyloxy group, a nicotinoyloxy group, an amino group or a 5- or 6-membered cyclic aromatic heterocyclic group containing 1 or 2 nitrogen atoms, oxygen atoms or sulfur atoms.) or a phenyl group; and 6) a compound wherein A is an ethylene group; far more preferably 7) a compound wherein $R^2$ is a $C_1$–$C_4$ alkyl group having a substituent (said substituent is a mercapto group, a $C_1$–$C_5$ alkanoylthio group, a $C_1$–$C_4$ alkoxycarbonylthio group, a (5-methyl-2-oxo-1,3-dioxolen-4-yl) methoxycarbonylthio group, a $C_6$–$C_{10}$ arylcarbonylthio group or a 5- or 6-membered aromatic heterocyclic carbonylthio group containing 1 nitrogen atom, oxygen atom or sulfur atom; and particularly preferably 8) a compound wherein $R^1$ is a hydrogen atom, or an acetyl, propionyl, butyryl, isobutyryl or pivaloyl group; and 9) a compound wherein $R^2$ is a mercaptomethyl, acetylthiomethyl, isobutyrylthiomethyl, pivaloylthiomethyl, benzoylthiomethyl or ethoxycarbonylthiomethyl group.

The compounds of the general formula (I):

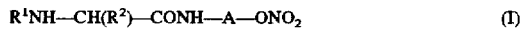

$$R^1NH-CH(R^2)-CONH-A-ONO_2 \qquad (I)$$

are preferably exemplified concretely by those listed below.

| Cmpd. No | $R^1$ | $R^2$ | A |
|---|---|---|---|
| 1 | H | PhCH$_2$ | CH$_2$CH$_2$ |
| 2 | H | Ph | CH$_2$CH$_2$ |
| 3 | H | 4-ThiaCH$_2$ | CH$_2$CH$_2$ |
| 4 | H | HSCH$_2$ | CH$_2$CH(CH$_3$) |
| 5 | H | HOCH$_2$ | CH$_2$CH(CH$_3$) |
| 6 | H | MeSCH$_2$ | CH$_2$CH(CH$_3$) |
| 7 | H | HSCH$_2$ | CH$_2$CH$_2$ |
| 8 | H | HOCH$_2$ | CH$_2$CH$_2$ |
| 9 | H | MeSCH$_2$ | CH$_2$CH$_2$ |
| 10 | H | MeSCH$_2$CH$_2$ | CH$_2$CH$_2$ |
| 11 | Ac | PhCH$_2$ | CH$_2$CH$_2$ |
| 12 | Ac | Ph | CH$_2$CH$_2$ |
| 13 | Ac | 4-ThiaCH$_2$ | CH$_2$CH$_2$ |
| 14 | Ac | MeSCH$_2$ | CH$_2$CH(CH$_3$) |
| 15 | Ac | HSCH$_2$ | CH$_2$CH(CH$_3$) |
| 16 | Ac | HOCH$_2$ | CH$_2$CH(CH$_3$) |
| 17 | Ac | HSCH$_2$ | CH$_2$CH$_2$ |
| 18 | Ac | HOCH$_2$ | CH$_2$CH$_2$ |
| 19 | Ac | MeSCH$_2$ | CH$_2$CH$_2$ |
| 20 | Ac | MeSCH$_2$CH$_2$ | CH$_2$CH$_2$ |
| 21 | Ac | AcSCH$_2$ | CH$_2$CH$_2$ |
| 22 | Ac | i-BurSCH$_2$ | CH$_2$CH$_2$ |
| 23 | Ac | PivSCH$_2$ | CH$_2$CH$_2$ |

-continued

| Cmpd. No | R¹ | R² | A |
|---|---|---|---|
| 24 | Ac | 2-PhPrpSCH₂ | CH₂CH₂ |
| 25 | Ac | EtOCOSCH₂ | CH₂CH₂ |
| 26 | Ac | PhCOSCH₂ | CH₂CH₂ |
| 27 | Ac | t-BuOCOSCH₂ | CH₂CH₂ |
| 28 | Ac | NicSCH₂ | CH₂CH₂ |
| 29 | Ac | i-NicSCH₂ | CH₂CH₂ |
| 30 | Nic | HSCH₂ | CH₂CH₂ |
| 31 | Nic | HOCH₂ | CH₂CH₂ |
| 32 | Nic | MeSCH₂ | CH₂CH₂ |
| 33 | Nic | MeSCH₂CH₂ | CH₂CH₂ |
| 34 | Nic | AcSCH₂ | CH₂CH₂ |
| 35 | Nic | i-BurSCH₂ | CH₂CH₂ |
| 36 | Nic | PivSCH₂ | CH₂CH₂ |
| 37 | Nic | NicSCH₂ | CH₂CH₂ |
| 38 | i-Nic | HSCH₂ | CH₂CH₂ |
| 39 | i-Nic | HOCH₂ | CH₂CH₂ |
| 40 | i-Nic | MeSCH₂ | CH₂CH₂ |
| 41 | i-Nic | MeSCH₂CH₂ | CH₂CH₂ |
| 42 | i-Nic | PivSCH₂ | CH₂CH₂ |
| 43 | i-Nic | i-BurSCH₂ | CH₂CH₂ |
| 44 | Piv | HSCH₂ | CH₂CH₂ |
| 45 | i-Bur | HSCH₂ | CH₂CH₂ |
| 46 | Piv | PivSCH₂ | CH₂CH₂ |
| 47 | i-Bur | i-BurSCH₂ | CH₂CH₂ |
| 48 | t-BuOCO | PhCH₂ | CH₂CH₂ |
| 49 | t-BuOCO | PhCH₂ | CH₂CH₂CH₂ |
| 50 | H | PhCH₂ | CH₂CH₂CH₂ |
| 51 | Ac | PhCH₂ | CH₂CH₂CH₂ |
| 52 | Nic | PhCH₂ | CH₂CH₂CH₂ |
| 53 | i-Nic | PhCH₂ | CH₂CH₂CH₂ |
| 54 | t-BuOCO | HSCH₂ | CH₂CH₂ |
| 55 | t-BuOCO | HSCH₂ | CH₂CH₂CH₂ |
| 56 | Ac | HSCH₂ | CH₂CH₂CH₂ |
| 57 | Nic | HSCH₂ | CH₂CH₂CH₂ |
| 58 | i-Nic | HSCH₂ | CH₂CH₂CH₂ |
| 59 | EtCO | HSCH₂ | CH₂CH₂ |
| 60 | EtCO | HOCH₂ | CH₂CH₂ |
| 61 | t-BuOCO | HOCH₂ | CH₂CH₂ |
| 62 | t-BuOCO | HOCH₂ | CH₂CH₂CH₂ |
| 63 | Ac | HOCH₂ | CH₂CH₂CH₂ |
| 64 | Nic | HOCH₂ | CH₂CH₂CH₂ |
| 65 | t-BuOCO | MeSCH₂ | CH₂CH₂ |
| 66 | EtCO | MeSCH₂ | CH₂CH₂ |
| 67 | H | MeSCH₂ | CH₂CH₂CH₂ |
| 68 | Ac | MeSCH₂ | CH₂CH₂CH₂ |
| 69 | Nic | MeSCH₂ | CH₂CH₂CH₂ |
| 70 | i-Nic | MeSCH₂ | CH₂CH₂CH₂ |
| 71 | t-BuOCO | 4-ThiaCH₂ | CH₂CH₂ |
| 72 | t-BuOCO | t-BuOCONH(CH₂)₄ | CH₂CH₂ |
| 73 | t-BuOCO | t-BuOCONH(CH₂)₄ | CH₂CH₂CH₂ |
| 74 | Ac | NH₂(CH₂)₄ | CH₂CH₂ |
| 75 | Nic | NH₂(CH₂)₄ | CH₂CH₂ |
| 76 | i-Nic | NH₂(CH₂)₄ | CH₂CH₂ |
| 77 | H | 4-OH-PhCH₂ | CH₂CH₂ |
| 78 | Ac | 4-OH-PhCH₂ | CH₂CH₂ |
| 79 | Nic | 4-OH-PhCH₂ | CH₂CH₂ |
| 80 | i-Nic | 4-OH-PhCH₂ | CH₂CH₂ |
| 81 | H | 4-OH-PhCH₂ | CH₂CH₂CH₂ |
| 82 | PhCH₂OCO | PhCH₂ | CH₂CH₂ |
| 83 | PhCH₂OCO | HOCH₂ | CH₂CH₂ |
| 84 | PhCH₂OCO | HSCH₂ | CH₂CH₂ |
| 85 | PhCH₂OCO | MeSCH₂ | CH₂CH₂ |
| 86 | Ac | 3-IndCH₂ | CH₂CH₂ |
| 87 | t-BuOCO | 4-ImdCH₂ | CH₂CH₂ |
| 88 | H | 4-ImdCH₂ | CH₂CH₂ |
| 89 | Nic | t-BuOCOSCH₂ | CH₂CH₂ |
| 90 | t-BuOCO | Ph | CH₂CH₂ |
| 91 | Ac | MeSCH₂CH₂ | CH₂CH₂CH₂ |
| 92 | Nic | MeSCH₂CH₂ | CH₂CH₂CH₂ |
| 93 | H | 3-IndCH₂ | CH₂CH₂ |
| 94 | Nic | 3-IndCH₂ | CH₂CH₂ |
| 95 | i-Nic | 3-IndCH₂ | CH₂CH₂ |
| 96 | Ac | 4-ImdCH₂ | CH₂CH₂ |
| 97 | Nic | 4-ImdCH₂ | CH₂CH₂ |
| 98 | i-Nic | 4-ImdCH₂ | CH₂CH₂ |
| 99 | Ac | 3-IndCH₂ | CH₂CH₂CH₂ |
| 100 | Ac | 4-ImdCH₂ | CH₂CH₂CH₂ |
| 101 | Ac | Mod-OCOSCH₂ | CH₂CH₂ |
| 102 | Nic | Mod-OCOSCH₂ | CH₂CH₂ |
| 103 | H | Mod-OCOSCH₂ | CH₂CH₂ |
| 104 | t-BuOCO | Mod-OCOSCH₂ | CH₂CH₂ |
| 105 | Ac | i-BuOCOSCH₂ | CH₂CH₂ |
| 106 | Nic | i-BuOCOSCH₂ | CH₂CH₂ |
| 107 | H | i-BuOCOSCH₂ | CH₂CH₂ |
| 108 | t-BuOCO | i-BuOCOSCH₂ | CH₂CH₂ |
| 109 | H | AcSCH₂ | CH₂CH₂ |
| 110 | H | PivSCH₂ | CH₂CH₂ |
| 111 | H | EtOCOSCH₂ | CH₂CH₂ |
| 112 | H | PhCOSCH₂ | CH₂CH₂ |
| 113 | H | i-BurSCH₂ | CH₂CH₂ |

In the above table, abbreviations stand for the following groups respectively.

Ac: acetyl

Bu: butyl

Bur: butyryl

Et: ethyl

Imd: imidazolyl

Ind: indolyl

Me: methyl

Mod: (5-methyl-2-oxo-1,3-dioxolen-4-yl)methyl

Nic: nicotinoyl

Ph: phenyl

Piv: pivaloyl

Pr: propyl

Prp: propionyl

Thia: thiazolyl

In the above table, preferred are compound Nos. 1, 2, 3, 7, 9, 10, 11, 12, 13, 17, 18, 19, 20, 21, 22, 23, 24, 25, 26, 27, 28, 29, 30, 33, 34, 46, 47, 48, 65, 66, 71, 78, 82, 85, 86, 87, 88, 89, 90, 96, 101, 102, 103, 105, 107, 109, 110, 111, 112 and 113, more preferably are compound Nos. 1, 7, 9, 10, 11, 17, 19, 20, 21, 23, 25, 26, 47, 101, 103, 109, 110, 111, 112 and 113, and particularly preferably are compound Nos.

7: N-(2-nitroxyethyl)-2-amino-3-mercaptopropanamide;

N-(2-nitroxyethyl)-2-acetylamino-3-mercaptopropanamide;

N-(2-nitroxyethyl)-2-acetylamino-3-acetylthiopropanamide;

N-(2-nitroxyethyl)-2-acetylamino-3-pivaloylthiopropanamide;

N-(2-nitroxyethyl)-2-acetylamino-3-ethoxycarbonylthiopropanamide;

N-(2-nitroxyethyl)-2-acetylamino-3-benzoylthiopropanamide; and

N-(2-nitroxyethyl)-2-isobutyrylamino-3-isobutyrylthiopropanamide; and

N-(2-nitroxyethyl)-2-acetylamino-3-(5-methyl-2-oxo-1,3-dioxolen-4-yl)methoxycarbonylthiopropanamide.

The compound having the general formula (I) of the present invention can easily be prepared according to the following procedures:

$$R^3NH-CH(R^4)-CO_2H + NH_2-A-ONO_2 \xrightarrow{\text{Step 1}}$$

$$\text{(II)} \qquad \text{(III)}$$

-continued

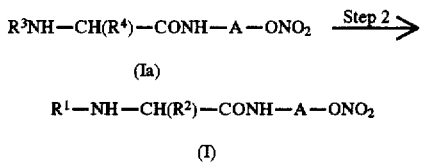

(Ia)

R¹—NH—CH(R²)—CONH—A—ONO₂

(I)

In the above scheme, $R^1$, $R^2$ and A have the same meanings as defined above; $R^3$ represents the same groups as defined for R except for hydrogen atom; and $R^4$ represents the same groups as defined for $R^2$ except that the amino or monoalkylamino group, alcoholic hydroxy group and mercapto groups included in $R^2$ are protected. While the protecting groups for the amino or monoalkyl group are not particularly limited so long as they are ordinarily used in the field of synthetic organic chemistry, they preferably include a t-butoxycarbonyl group or a halogenoacetyl group (i.e., chloroacetyl, bromoacetyl, iodoacetyl etc.,). The protecting groups for the alcoholic hydroxy group are not particularly limited so long as they are ordinarily used in the field of synthetic organic chemistry, they preferably include a tetrahydropyranyl group and tri-($C_1$–$C_4$ alkyl)silyl group (particularly t-butyldimethylsilyl group). In addition, while the protecting groups for mercapto group are not particularly limited so long as they are ordinarily used in the field of synthetic organic chemistry, they preferably include a t-butoxycarbonyl group, a $C_1$–$C_4$ alkylthio group or a $C_6$–$C_{10}$ arylthio group.

Step 1 is for preparing a compound having the general formula (Ia), and it is accomplished by reacting a compound having the general formula (II) or its reactive derivative with a compound having the general formula (III) in an inert solvent. For example, the step is carried out by the acid halide method, mixed acid anhydride method, active ester method or condensation method.

The acid halide method is carried out by reacting the compound having the general formula (II) with a halogenating agent (e.g. thionyl chloride, phosphorus pentachloride, etc.) to prepare an acid halide, followed by reacting the acid halide with the compound of the general formula (III) in an inert solvent in the absence or presence of a base.

The base employable includes, for example, organic amines such as triethylamine, N-methylmorpholine, pyridine and 4-dimethylaminopyridine, alkali metal bicarbonates such as sodium bicarbonate and potassium bicarbonate, or alkali metal carbonates such as sodium carbonate and potassium carbonate, preferably organic amines.

The inert solvent employable is not particularly limited so long as it does not participate in the reaction and includes, for example, hydrocarbons such as hexane, cyclohexane, benzene, toluene and xylene, halogenated hydrocarbons such as dichloromethane, 1,2-dichloroethane and carbon tetrachloride, ethers such as ether, tetrahydrofuran and dioxane, ketones such as acetone, amides such as N,N-dimethylformamide, N,N-dimethylacetamide, N-methyl-2-pyrrolidone and hexamethylphosphoramide, or sulfoxides such as dimethyl sulfoxide, and preferably hydrocarbons, halogenated hydrocarbons, ethers or amides.

While the reaction temperature varies depending on the starting compounds (II) and (III) and the kinds of solvent, the reaction temperatures for the reaction of the halogenating agent with the compound (II), and for the reaction of the acid halide with the compound (III) are both usually at −20° to 150° C. The reaction temperature for the reaction of the halogenating agent and the compound (III) is preferably at around room temperature and that for the reaction of the acid halide with the compound (III) is preferably at 0° C. to 100° C. The reaction time varies depending on the reaction temperature and so on and it is 30 minutes to 24 hours (preferably 1 to 5 hours).

The mixed acid anhydride method is carried out by reacting a lower alkyl halogenocarbonate or di-lower alkylcyanophosphonate with the compound (II) to prepare a mixed acid anhydride, followed by reacting the anhydride with the compound (III).

The reaction for preparing the mixed acid anhydride is carried out by reacting a lower alkyl halogenocarbonate such as ethyl chlorocarbonate and isobutyl chlorocarbonate or a di-lower alkylcyanophosphonate such as diethylcyanophosphonate with the compound (II), and it is preferably carried out in an inert solvent in the presence of a base.

The base and inert solvent employable are the same as those used in the above acid halide method.

While the reaction temperature varies depending on the starting compound (II) and the kind of solvent, it is usually −20° C. to 50° C. (preferably 0° C. to 30° C.). While the reaction time also varies depending on the reaction temperature and so on, it is usually 30 minutes to 24 hours (preferably 1 to 5 hours).

The reaction of the mixed acid anhydride with the compound (III) is preferably carried out in an inert solvent in the absence or presence of a base, and the base and inert solvent employable are the same as those used in the above acid halide method.

While the reaction temperature varies depending on the starting compound (III) and the kind of solvent, it is usually −20° C. to 100° C. (preferably 0° C. to 50° C). While the reaction time also varies depending on the reaction temperature and so on, it is usually 30 minutes to 24 hours (preferably 1 to 10 hours).

This method can be also achieved in the coexistence of the lower alkyl haloggenocarbonate or di-lower alkylcyanophosphonate and the compound (III).

The active ester method is carried out by reacting the compound (II) with an active esterification agent (e.g. N-hydroxy compounds such as N-hydroxysuccinimide and N-hydroxybenzotriazole, etc.,) in the presence of a condensation agent (e.g. dicyclohexylcarbodiimide, carbonyldiimidazole, etc.) to prepare an active ester, followed by reacting the active ester with the compound (III).

The reaction for preparing the active ester is preferably carried out in an inert solvent, and the inert solvent employable is the same as that used in the above acid halide method.

While the reaction temperature varies depending on the starting compounds (II) and (III) and the kind of solvent, it is usually −20° C. to 50° C. (preferably −10° C. to 30° C.) for the active esterification reaction: whereas it is −20° C. to 50° C. (preferably 0° C. to 30° C.) for the reaction of the active ester compound with the compound (III). While the reaction time also varies depending on the reaction temperature and so on, it is 30 minutes to 24 hours (preferably 1 to 10 hours) for the both reactions.

The condensation method is carried out by reacting the compounds (II) and (III) directly in the presence of a condensation agent (e.g. dicyclohexylcarbodiimide, carbonyldiimidazole, 1-(N,N-dimethylaminopropyl)-3-ethylcarbodiimide hydrochloride, etc.). This reaction is carried out in the same manner as in the preparation of the said active ester, and reaction time is usually from 30 minutes to 30 hours (preferably 1 to 18 hours).

After completion of the reaction, the desired products in the respective reactions are collected from the reaction mixtures according to the conventional method. For example, the desired product can be obtained by filtration of the crystals precipitated from the reaction mixture; or after addition of water to the reaction mixture, by extracting with a water-immiscible organic solvent such as ethyl acetate, drying the extract and evaporating the extraction solvent. The thus obtained products can further be purified by conventional methods such as recrystallization and column chromatography, if necessary.

The starting compound (II) may be a known compound or can easily be prepared according to known methods [e.g. J. Med. Chem., 11, 625 (1968)].

Step 2 is for preparing the compound (I) by eliminating the t-butoxycarbonyl group which is the protecting group for the amino group included in $R^3$ or/and the protecting group for the amino group, monoalkylamino group, alcoholic hydroxy group or mercapto group. While the reaction for eliminating the protecting group varies depending on the kind of protecting group, it is carried out by methods employed usually in the field of synthetic organic chemistry.

For example, when the protecting group for the amino group or alkylamino group is a t-butoxycarbonyl group, it can be eliminated by reacting the corresponding compound (Ia) with an acid (e.g. mineral acids such as hydrochloric acid, sulfuric acid and nitric acid or organic acids such as acetic acid, trifuloroacetic acid, methanesulfonic acid and p-toluenesulfonic acid) in an inert solvent (e.g. ethers such as ether, tetrahydrofuran and dioxane, halogenated hydrocarbons such as dichloromethane and 1,2-dichloroethane or aromatic hydrocarbons such as benzene, toluene and xylene) at 0° C. to 50° C. (preferably at around room temperature) for 30 minutes to 24 hours (preferably for 1 hour to 16 hours). Meanwhile, in the cases where the protecting group for the hydroxy group is a tetrahydropyranyl group or the protecting group for the mercapto group is a t-butoxycarbonyl group, such protecting groups can be eliminated in the same manner as described above.

When the protecting group for the amino group or alkylamino group is a halogenoacetyl group, it can be eliminated by reacting the corresponding compound (Ia) with thiourea in an inert solvent (e.g. amides such as dimethylformamide and dimethylformacetamide or sulfoxides such as dimethyl sulfoxide) at 0° C. to 50° C. (preferably at around room temperature) for 30 minutes to 5 hours (preferably for 1 hour to 2 hours).

When the protecting group for the hydroxy group is a silyl group, it can be eliminated by reacting the corresponding compound (Ia) with tetra($C_1$–$C_4$ alkyl)ammonium halide (particularly tetrabutylammonium fluoride) in an inert solvent (e.g. ethers such as ether, tetrahydrofuran and dioxane or nitriles such as acetonitrile) at 0° C. to 50° C. (preferably at around room temperature) for 30 minutes to 5 hours (preferably for 1 hour to 2 hours).

When the protecting group for the mercapto group is a $C_1$–$C_4$ alkylthio group or a $C_6$–$C_{10}$ arylthio group, it can be eliminated by reacting the corresponding compound (Ia) with a mercapto compound (e.g. thiophenol, mercaptoacetic acid, mercaptoethanol, etc.) in an inert solvent (e.g. water, ethers such as ether, tetrahydrofuran and dioxane, alcohols such as methanol and ethanol or a mixture thereof) at 0° C. to 50° C. (preferably at around room temperature) for 30 minutes to 5 hours (preferably for 1 hour to 2 hours).

After completion of the reaction, the desired products in the respective reactions are collected from the reaction mixtures according to the conventional method. For example, the desired product can be obtained by neutralization, as necessary, of the reaction mixture and collection of the crystals precipitated from the reaction mixture by filtration: or after addition of water to the reaction mixture, by extracting with a water-immiscible organic solvent such as ethyl acetate, drying the extract and evaporating the extraction solvent. The thus obtained products can further be purified by conventional methods such as recrystallization and column chromatography, if necessary.

Based on the tests carried out using carotid collateral vessel system in anesthetized dogs, the compound of the above-mentioned general formula (I) of the present invention was proved to have strong vasodilator action for collateral vessels, to hardly undergo the first-pass effect and to have less drug tolerance. Therefore, the present compound is extremely useful as a prophylactic and therapeutic drug for angina perctoris.

(TEST EXAMPLE 1)

Test method for vasodilator action of collateral vessels

Beagle dogs (male) weighing 9 to 13 kg were anesthetized with intravenous injection of 30 mg/kg of pentobarbital and experiments were carried out under artificial respiration. For measuring left carotid arterial pressure, a polyethylene canula (atom venous catheter 2F) was inserted retrogradably to the one francle of the left thyroidal artery. The left carotid artery, upstream of the pressure measuring site, was occluded with an arterial forceps for one minute. The pressure immediately before the occlusion (P) and the peripheral pressure reduction by the occlusion (ΔP) were measured. Next, the drug to be tested was administered through the polyethylene canula inserted to the femoral vein, and the left carotid artery was occluded again for one minute after 5, 15, 30, 45 and 60 minutes, respectively. The pressure immediately before the occlusion (P') and the peripheral pressure reduction by the occlusion (ΔP') were measured. The vasodilation action for the collateral vessels (Collateral Index=CI) was determined according to the following scheme:

$$100-(\Delta P'/P')\times 100/(\Delta P/P).$$

According to this test, the compounds of Examples 2, 3, 7 and 10 exhibited excellent vasodilator action for collateral vessels.

When the compound (I) is used as a therapeutic drug for angina pectoris, it can be administered orally or parenterally per se or as a pharmaceutical composition in the form of powder, granule, tablet, capsule, injection, etc. obtained by mixing the compound (I) with an appropriate pharmacologically acceptable carrier, vehicle, diluting agent, etc. While the dose varies depending on the condition of the diseases to be treated and the administration method, it is usually administered in an amount of 1 to 1000 mg at a dose, particularly about 5 to 300 mg for oral administration; whereas in an amount of about 0.1 to 100 mg, particularly about 0.5 to 50 mg at a dose for intravenous administration, and such dose of drug is desirably administered 1 to 3 times a day depending on the conditions.

Best mode for practicing the Invention

The present invention will be described below more specifically by Examples and Reference examples, but the scope of the present invention is not limited thereto.

(Example 1)

(2R)-N-(2-Nitrooxyethyl)-2-acetylamino-3-tert-butoxycarbonylthiopropanamide (Exemplary compound No. 27)

In 100 ml of anhydrous tetrahydrofuran were suspended 1.32 g of (2R)-2-acetylamino-3-tertbutoxycarbonylthiopropionic acid and 0.93 g of 2-nitrooxyethylamine nitrate, and to the resulting suspension were added 2.8 ml of triethylamine and 0.9 ml of diethyl cyanophosphonate with ice-cooling. The mixture was stirred at room temperature for 4 hours. To the residue obtained by evaporation of the solvent under reduced pressure was added ethyl acetate. The resulting mixture was washed successively with water and aqueous sodium chloride and dried over anhydrous magnesium sulfate, and the solvent was removed by evaporation. The resulting yellow oil was purified by column chromatography through silica gel using ethyl acetate-dichloromethane (1:1) as an eluent to obtain colorless crystals. They were further recrystallized from isopropyl ether to give 1.33 g of the title compound as colorless needles.

m.p. 96°–97° C.

NMR spectrum (CDCl$_3$) δ ppm:

1.50(9H, s), 2.02(3H, s), 3.20(2H, d, J=6 Hz), 3.59(2H, dd, J=6, 11 Hz), 4.55(2H, t, J=5 Hz), 4.67(1H, dd, J=6, 13 Hz), 6.81(1H, d, J=7 Hz), 7.43(1H, t, J=6 Hz).

(Example 2)

(2R)-N-(2-Nitrooxyethyl)-2-acetylamino-3-mercaptopropanamide (Exemplary compound No. 17)

In 10 ml of 4N-hydrogen chloride/dioxane was dissolved 1.23 g of the compound of Example 1, and the resulting solution was left to stand at room temperature overnight. To the residue obtained by evaporation of the solvent under reduced pressure was added ethyl acetate, and the mixture was washed successively with a saturated aqueous sodium bicarbonate and aqueous sodium chloride and dried over anhydrous magnesium sulfate. The solvent was removed by evaporation. The resulting yellow oil was purified by column chromatography through silica gel using ethyl acetate-dichloromethane (2:1) as an eluent to obtain colorless crystals. They were further recrystallized from isopropyl ether to give 0.13 g of the title compound as colorless needles.

m.p. 103°–104° C.

NMR spectrum (CDCl$_3$) δ ppm:

1.65(1H, dd, J=7, 10 Hz), 2.06(3H, s), 2.73–2.84(1H, m), 2.93–3.03(1H, m), 3.63(2H, dd, J=5, 11 Hz), 4.57(2H, t, J=5 Hz), 4.66–4.74(1H, m), 6.75(1H, d, J=8 Hz), 7.48(1H, t, J=5 Hz).

(Example 3)

(2R)-N-(2-Nitrooxyethyl)-2-acetylamino-3-acetylthiopropanamide (Exemplary compound No. 21)

In 20 ml of anhydrous tetrahydrofuran were suspended 1.0 g of (2R)-2-acetylamino-3-acetylthiopropionic acid and 0.82 g of 2-nitrooxyethylamine nitrate, and to the resulting suspension were added 2.0 ml of triethylamine and 0.95 ml of diethyl cyanophosphonate with ice-cooling. The mixture was stirred at room temperature for 2.5 hours. To the residue obtained by evaporation of the solvent under reduced pressure was added ethyl acetate, and the resulting mixture was washed with water and aqueous sodium chloride and dried over anhydrous magnesium sulfate. The solvent was removed by evaporation. The resulting yellow oil was purified by column chromatography through silica gel using ethyl acetate as an eluent to give 1.0 g of the title compound as colorless crystals.

m.p. 95°–97° C.

NMR spectrum (CDCl$_3$) δ ppm:

2.02(3H, s), 2.38(3H, s), 3.27–3.35(2H, m), 3.56–3.63 (2H, m), 4.52–4.65(3H, m), 6.57(1H, d, J=7 Hz), 7.21(1H, bs).

(Example 4)

(2R)-N-(2-Nitrooxyethyl)-2-acetylamino-3-benzoylthiopropanamide (Exemplary compound No. 26)

In 20 ml of anhydrous tetrahydrofuran were suspended 0.90 g of (2R)-2-acetylamino-3-benzoylthiopropionic acid and 0.68 g of 2-nitrooxyethylamine nitrate, and to the resulting suspension were added 1.4 ml of triethylamine and 0.66 ml of diethyl cyanophosphonate with ice-cooling. The mixture was stirred at room temperature for 4 hours. To the residue obtained by evaporation of the solvent under reduced pressure was added ethyl acetate, and the resulting mixture was washed successively with water and aqueous sodium chloride and dried over anhydrous magnesium sulfate. The solvent was removed by evaporation. The resulting yellow crystals were purified by column chromatography through silica gel using ethyl acetate as an eluent to give 0.84 g of the title compound as colorless crystals.

m.p. 137°–138° C. (decomp.).

NMR spectrum (CDCl$_3$+DMSO-d$_6$) δ ppm:

2.00(3H, s), 3.49(2H, d, J=6 Hz), 3.58(2H, dd, J=5, 10 Hz), 4.54(2H, t, J=5 Hz), 4.72(1H, dd, J=6, 14 Hz), 6.98(1H, d, J=7 Hz), 7.46(2H, t, J=7 Hz), 7.60(1H, t, J=7 Hz), 7.70(1H, bs), 7.95(2H, d, J=7 Hz).

(Example 5)

(2R)-N-(2-Nitrooxyethyl)-2-acetylamino-3-methylthiopropanamide (Exemplary compound No. 19)

In 20 ml of anhydrous tetrahydrofuran were suspended 1.0 g of (2R)-2-acetylamino-3-methylthiopropionic acid and 1.14 g of 2-nitrooxyethylamine nitrate, and to the resulting suspension were added 2.4 ml of triethylamine and 1.1 ml of diethyl cyanophosphonate with ice-cooling. The mixture was stirred at room temperature for 2.5 hours. To the residue obtained by evaporation of the solvent under reduced pressure was added ethyl acetate, and the resulting mixture was washed successively with water and aqueous sodium chloride and dried over anhydrous magnesium sulfate. The solvent was removed by evaporation. The resulting pale yellow crystals were washed with isopropyl ether and dried to give 0.44 g of the title compound as pale yellow crystals.

m.p. 93°–95° C.

NMR spectrum (CDCl$_3$) δ ppm:

2.05(3H, s), 2.16(3H, s), 2.76–2.93(2H, m), 3.63(2H, dd, J=6, 11 Hz), 4.54–4.64(3H, m), 6.56(1H, d, J=7 Hz), 7.27 (1H, bs).

(Example 6)

(2R)-N-(2-Nitrooxyethyl)-2-acetylamino-3-pivaloylthiopropanamide (Exemplary compound No. 23)

The procedures of Example 1 were analogously repeated using 0.70 g of (2R)-2-acetylamino-3-pivaloylthiopropionic acid and 574 mg of 2-nitrooxyethylamine nitrate to give 0.72 g of the title compound as colorless crystals.

m.p. 101°–103° C.

NMR spectrum (CDCl$_3$) δ ppm:

1.25(9H, s), 2.00(3H, s), 3.18–3.34(2H, m), 3.59(2H, dd, J=6, 11 Hz), 4.48–4.56(3H, m), 6.43(1H, d, J=7 Hz), 6.94 (1H, t, J=6 Hz).

(Example 7)

(2R)-N-(2-Nitrooxyethyl)-2-acetylamino-3-ethoxycarbonylthiopropanamide (Exemplary compound No. 25)

The procedures of Example 1 were analogously repeated using 350 mg of (2R)-2-acetylamino-3-ethoxycarbonylthiopropionic acid and 302 mg of 2-nitrooxyethylamine nitrate to give 190 mg of the title compound as colorless crystals.

m.p. 119°–120° C.

NMR spectrum (CDCl$_3$) δ ppm:

1.32(3H, t, J=7 Hz), 2.04(3H, s), 3.25(2H, d, J=7 Hz), 3.60(2H, dd, J=6, 11 Hz), 4.30(2H, q, J=7 Hz), 4.50–4.70 (3H, m), 6.55(1H, d, J=5 Hz), 6.96(1H, bs).

(Example 8)

(2R)-N-(2-Nitrooxyethyl)-2-acetylamino-3-(2-phenylpropionyl)thiopropanamide (Exemplary compound No. 24)

The procedures of Example 1 were analogously repeated using 1.33 g of (2R)-2-acetylamino-3-(2-phenylpropionyl)thiopropionic acid and 0.91 g of 2-nitrooxyethylamine nitrate to give 0.60 g of the title compound as colorless crystals.

m.p. 75°–77° C.

NMR spectrum (CDCl$_3$) δ ppm:

1.54(3H, d, J=7 Hz), 1.80(3H, s), 1.90(3H, s), 3.13–3.34 (2H, m), 3.43–3.58(2H, m), 3.88–3.97(1H, m), 4.42–4.59 (3H, m), 6.38(1H, t, J=7 Hz), 7.03(1H, d, J=6 Hz), 7.29–7.37 (5H, m).

(Example 9)

(2R)-N-(2-Nitrooxyethyl)-2-tert-butoxycarbonylamino-3-methylthiopropanamide (Exemplary compound No. 65)

The procedures of Example 1 were analogously repeated using 2.0 g of (2R)-2-tert-butoxycarbonylamino-3-methylthiopropionic acid and 1.72 g of 2-nitrooxyethylamine nitrate to give 1.04 g of the title compound as colorless crystals.

m.p. 66°–68° C.

NMR spectrum (CDCl$_3$) δ ppm:

1.46(9H, s), 2.15(3H, s), 2.78–2.97(2H, m), 3.61–3.67 (2H, m), 4.26(1H, dd, J=7, 13 Hz), 4.55(2H, t, J=5 Hz), 5.37(1H, d, J=7 Hz), 6.88(1H, bs).

(Example 10)

(2R)-N-(2-Nitrooxyethyl)-2-amino-3-methylthiopropanamide hydrochloride (Exemplary compound No. 9)

In 10 ml of 4N-hydrogen chloride/dioxane solution was dissolved 0.78 g of (2R)-N-(2-nitrooxyethyl)-2-tert-butoxycarbonylamino-3-methylthiopropanamide, and the resulting mixture was stirred at room temperature for 1 hour. The solvent was evaporated under reduced pressure to give 0.53 g of the title compound as a pale yellow foam.

NMR spectrum (CDCl$_3$+DMSO-d$_6$) δ ppm:

2.23(3H, s), 3.14(2H, bs), 3.65(2H, bs), 4.43(1H, bs), 4.63(2H, s), 7.90–8.90(3H, bs), 9.04(1H,s).

(Example 11)

(2R)-N-(2-Nitrooxyethyl)-2-pivaloylamino-3-pivaloylthiopropanamide (Exemplary compound No. 46)

The procedures of Example 1 were analogously repeated using 1.0 g of (2R)-2-pivaloylamino-3-pivaloylthiopropionic acid and 0.701 g of 2-nitrooxyethylamine nitrate to give 0.23 g of the title compound as colorless crystals.

m.p. 56°–58° C.

NMR spectrum (CDCl$_3$) δ ppm:

1.18(9H, s), 1.25(9H, s), 3.22(1H, dd, J=4, 15 Hz), 3.37(1H, dd, J=9, 15 Hz), 3.54–3.63(2H, m), 4.44–4.55(3H, m), 6.62(1H, d, J=6 Hz), 7.10(1H, bs).

(Example 12)

(2R)-N-(2-Nitrooxyethyl)-2-nicotinoylamino-3-tert-butoxycarbonylthiopropanamide (Exemplary compound No. 89)

The procedures of Example 1 were analogously repeated using 360 mg of (2R)-2-nicotinoylamino-3-tert-butoxycarbonylthiopropionic acid and 203 mg of 2-nitrooxyethylamine nitrate to give 243 mg of the title compound as a colorless foam.

NMR spectrum (CDCl$_3$) δ ppm:

1.45(9H, s), 3.25–3.53(2H, m), 3.55–3.67(2H, m), 4.56 (2H, t, J=5 Hz), 4.82–4.96(1H, m), 7.36(1H, dd, J=5, 8 Hz), 7.66(1H, t, J=6 Hz), 7.89(1H, d, J=7 Hz), 8.14(1H, d, J=5 Hz), 8.73(1H, d, J=3 Hz), 9.05(1H, d, J=2 Hz).

(Example 13)

(2R)-N-(2-Nitrooxyethyl)-2-nicotinoylamino-3-mercaptopropanamide (Exemplary compound No. 30)

In 1 ml of 4N-hydrogen chloride/dioxane solution was dissolved 223 mg of (2R)-N-(2-nitrooxyethyl)-2-nicotinoylamino-3the t-butoxycarbonylthiopropanamide, and the resulting solution was stirred at room temperature for 2 hours and 15 minutes. The solvent was evaporated under reduced pressure, and the residue was neutralized with aqueous sodium hydrogencarbonate. The mixture was extracted with ethyl acetate, and the solvent was evaporated under reduced pressure. The residue was purified by column chromatography through silics gel using ethyl acetate as an eluent and recrystallized from isopropyl ether-dichloromethane to give 74 mg of the title compound as white needles.

m.p. 99°–100° C.

NMR spectrum (CDCl$_3$) δ ppm:

1.76(1H, t, J=5 Hz), 2.87–3.02(1H, m), 3.10–3.20(1H, m), 3.60–3.80(2H, m), 4.59(2H, t, J=5 Hz), 4.89(1H, dd, J=7, 13 Hz), 7.35–5.53(2H, m), 7.63(1H, d, J=7 Hz), 8.10–8.20(1H, m), 8.73–8.83(1H, m), 9.08(1H, s).

(Example 14)

(2S)-N-(2-Nitrooxyethyl)-2-acetylamino-4-methylthiobutanamide (Exemplary compound No. 20)

The procedures of Example 1 were analogously repeated using 1.00 g of N-acetyl-L-methionine and 1.06 g of 2-nitrooxyethylamine nitrate to give 1.18 g of the title compound as colorless crystals.

m.p. 95°–97° C.

NMR spectrum (CDCl$_3$) δ ppm:

1.90–2.15(2H, m), 2.02(3H, s), 2.11(3H, s), 2.46–2.65 (2H, m), 3.52–3.72(2H, m), 4.55(2H, t, J=5 Hz), 4.65(1H, dd, J=7, 15 Hz), 6.59(1H, d, J=5 Hz), 7.34(1H, bs).

(Example 15)

(2R)-N-(2-Nitrooxyethyl)-2-isobutyrylamino-3-isobutyrylthiopropanamide (Exemplary compound No. 47)

The procedures of Example 1 were analogously repeated using 0.45 g of (2R)-2-isobutyrylamino-3-isobutyrylthiopropionic acid and 0.35 g of 2-nitrooxyethylamine nitrate to give 0.55 g of the title compound as pale yellow crystals.

m.p. 64°–66° C.

NMR spectrum (CDCl$_3$) δ ppm:

1.13(3H, s), 1.15(3H, s), 1.19(3H, s), 1.21(3H, s), 2.30–2.47(1H, m), 2.72–2.87(1H, m), 3.15–3.40(2H, m), 3.50–3.70(2H, m), 4.47–4.63(3H, m), 6.51(1H, d, J=7 Hz), 7.20(1H, bs).

(Example 16)

(2S)-N-(2-Nitrooxyethyl)-2-acetylamino-3-hydroxypropanamide (Exemplary compound No. 18)

(a) (2R)-N-(2-Nitrooxyethyl)-2-acetylamino-3-(tetrahydropyran-2-yl)oxypropanamide The procedures of Example 1 were analogously repeated using 1.07 g of (2S)-2-acetylamino-3-(tetrahydropyran-2-yl)oxypropionic acid and 0.94 g of 2-nitrooxyethylamine nitrate to give 0.44 g of the title compound as pale yellow crystals.

m.p. 93°–95° C.

NMR spectrum (CDCl$_3$+DMSO-d$_6$) δ ppm:

1.42–1.90(6H, m), 2.035(3H, s), 2.05(3H, 3.45–4.03(6H, m), 4.45–4.73(4H, m), 6.739(1H, d), 6.89(1H, d), 7.30(1H, bs), 7.44(1H, bs).

(b) (2S)-N-(2-Nitrooxyethyl)-2-acetylamino-3-hydroxypropanamide

In 5 ml of 4N-hydrogen chloride/dioxane solution was dissolved 0.42 g of (2S)-N-(2-nitrooxyethyl)-2-acetylamino-3-(tetrahydropyran-2-yl)oxypropanamide, and the resulting solution was stirred at room temperature for 1 hour. The solvent was evaporated under reduced pressure, and the residue was neutralized with aqueous sodium hydrogencarbonate. The mixture was extracted with ethyl acetate, and the solvent was evaporated under reduced pressure. The residue was purified by column chromatography through silica gel using ethyl acetate as an eluent and recrystallized from ethyl acetate to give 48 mg of the title compound as colorless crystals.

m.p. 91°–93° C.

NMR spectrum (CDCl$_3$+DMSO-d$_6$) δ ppm:

2.05(3H, s), 3.50–3.70(3H, m), 3.90–4.10(2H, m), 4.40–4.50(1H, m), 4.56(2H, t, J=5 Hz), 6.92(1H, bs), 7.56 (1H, bs).

(Example 17)

(2S)-N-(2-Nitrooxyethyl)-2-acetylamino-3-(indol-3-yl)propanamide (Exemplary compound No. 86)

The procedures of Example 1 were analogously repeated using 500 mg of N-acetyl-L-triptophane and 355 mg of 2-nitrooxyethylamine nitrate to give 270 mg of the title compound as colorless crystals.

m.p. 108°–110° C.

NMR spectrum (CDCl$_3$) δ ppm:

1.89(3H, s), 3.05–3.30(3H, m), 3.35–3.53(1H, m), 4.00–4.12(1H, m), 4.15–4.30(1H, m), 4.75(1H, dd, J=7, 15 Hz), 6.80–7.15(5H, m), 7.28(1H, d, J=5 Hz), 7.55(1H, d, J=7 Hz), 8.52(1H, s).

(Example 18)

(2S)-N-(2-Nitrooxyethyl)-2-tert-butoxycarbonylamino-3-phenylpropanamide (Exemplary compound No. 48)

The procedures of Example 1 were analogously repeated using 1.0 g of (2S)-2-tert-butoxycarbonylamino-3-phenylpropionic acid and 0.70 g of 2-nitrooxyethylamine nitrate to give 1.09 g of the title compound as colorless crystals.

m.p. 121°–123° C.

NMR spectrum (CDCl$_3$) δ ppm:

1.42(9H, s), 2.97–3.17(2H, m), 3.38–3.65(2H, m), 4.25–4.48(3H, m), 5.01(1H, bs), 6.11(1H, bs), 7.15–7.48 (5H, m).

(Example 19)

(2S)-N-(2-Nitrooxyethyl)-2-amino-3-phenylpropanamide hydrochloride (Exemplary compound No. 1)

In 5 ml of 4N-hydrogen chloride/dioxane solution was dissolved 0.50 g of (2S)-N-(2-nitrooxyethyl)-2-tert-butoxycarbonylamino-3-phenylpropanamide, and the resulting solution was allowed to stand at room temperature over night. The solvent was evaporated under reduced pressure and the residue was crystallized from isopropyl ether to give 0.36 g of the title compound as white crystals.

m.p. 148°–150° C.

NMR spectrum (CDCl$_3$+DMSO-d$_6$) δ ppm:

3.10–3.70(4H, m), 4.23(1H, bs), 4.32–4.53(2H, m), 7.20–7.42(5H, m), 8.76(1H, bs).

(Example 20)

(2S)-N-(Nitrooxyethyl)-2-tert-butoxycarbonylamino-2-phenthylacetamide (Exemplary compound No. 90)

The procedures of Example 1 were analogously repeated using 500 mg of (2S)-2-tert-butoxycarbonylamino-2-phenylacetic acid and 370 mg of 2-nitrooxyethylamine nitrate to give 560 mg of the title compound as a yellow oil.

NMR spectrum (CDCl$_3$) δ ppm:

1.41(9H, s), 3.50–3.65(2H, m), 4.49(2H, t, J=5 Hz), 5.13(1H, bs), 5.65(1H, bs), 6.19(1H, bs), 7.35(5H, s).

(Example 21)

(2S)-N-(2-Nitrooxyethyl)-2-amino-2-phenylacetamide hydrochloride (Exemplary compound No. 2)

The procedures of Example 1 were analogously repeated using 560 mg of (28)-N-(2-nitrooxyethyl)-2-tert-butoxycarbonylamino-2-phenylacetamide and 5 ml of 4N-hydrogen chloride/dioxane solution to give 230 mg of the title compound as a yellow oil.

NMR spectrum (CDCl$_3$+DMSO-d$_6$) δ ppm:

3.40–3.65(2H, m), 4.40–4.60(2H, m), 5.37(1H, s), 7.25–7.47(3H, m), 7.60–7.75(2H, m), 8.90(1H, bs).

(Example 22)

(2S)-N-(2-Nitrooxyethyl)-2-tert-butoxycarbonylamino-3-(4-thiazolyl)propamide (Exemplary compound No. 71)

The procedures of Example 1 were analogously repeated using 1.0 g of (2S)-2-tert-butoxycarbonylamino-3-(4-thiazolyl)propionic acid and 683 mg of 2-nitrooxyethylamine nitrate to give 400 mg of the title compound as white crystals.

m.p. 82°–84° C.

NMR spectrum (CDCl$_3$) δ ppm:

1.46(9H, s), 3.18(1H, dd, J=5, 15 Hz), 3.32–3.68(3H, m), 4.28–4.45(2H, m), 4.53(1H, bs), 6.13(1H, d, J=7 Hz), 6.90 (1H, bs), 7.11(1H, s), 8.76(1H, s).

(Example 23)

(2S)-N-(2-Nitrooxyethyl)-2-amino-3-(4-thiazolyl) propanamide hydrochloride (Exemplary compound No. 3)

The procedures of Example 10 were analogously repeated using 400 mg of (2S)-N-(2-nitrooxyethyl)-2-tert-butyloxycarbonylamino-3-(4-thiazolyl)propanamide and 5 ml of 4N-hydrogen chloride/dioxane solution to give 350 mg of the title compound as white crystals.

m.p. 154°–157° C.

NMR spectrum (CDCl$_3$+DMSO-d$_6$) δ ppm:

3.40–3.70(4H, m), 4.32(1H, bs), 4.53(2H, t, J=5 Hz), 7.51(1H, s), 9.00(1H, s), 9.10(1H, bs).

(Example 24)

(2S)-N-(2-Nitrooxyethyl)-2-acetylamino-3-(4-hydroxyphenyl)propanamide (Exemplary compound No. 78)

The procedures of Example 1 were analogously repeated using 400 mg of (2S)-2-acetylamino-3-(4-hydroxyphenyl) propionic acid and 345 mg of 2-nitrooxyethylamine nitrate to give 260 mg of the title compound as colorless crystals.

m.p. 130°–131° C.

NMR spectrum (CDCl$_3$+DMSO-d$_6$) δ ppm:

1.96(3H, s), 2.93(2H, d, J=7 Hz), 3.35–3.62(2H, m), 4.32–4.52(2H, m), 4.60(1H, dd, J=7, 15 Hz), 6.74(2H, d, J=5 Hz), 6.86(1H, d, J=5 Hz), 7.01(2H, d, J=9 Hz), 7.36(1H, bs), 8.59(1H, bs).

(Example 25)

(2S)-N-(2-Nitrooxyethyl)-2-tert-butoxycarbonylamino-3-(4-imidazol)propanamide (Exemplary compound No. 87)

The procedures of Example 1 were analogously repeated using 1.0 g of (2S)-2-tert-butoxycarbonylamino-3-(4-imidazolyl)propionic acid and 730 mg of 2-nitrooxyethylamine nitrate to give 660 mg of the title compound as white crystals.

m.p. 104°–106° C.

NMR spectrum (CDCl$_3$+DMSO-d$_6$) δ ppm:

1.44(9H, s), 2.70–3.20(2H, m), 3.40–3.65(2H, m), 4.30–4.50(3H, m), 6.20(1H, d, J=7 Hz), 6.81(1H, bs), 7.52 (2H, bs).

(Example 26)

(2S)-N-(2-Nitrooxyethyl)-2-amino-3-(4-thiazolyl) propanamide dihydrochloride (Exemplary compound No. 88)

The procedures of Example 10 were analogously repeated using 380 mg of (2S)-N-(2-nitrooxyethyl)-2-tert-butoxycarbonylamino-3-(4-imidazolyl)propanamide and 5 ml of 4N-hydrogen chloride/dioxane solution to give 215 mg of the title compound as a yellow foam.

NMR spectrum (D$_2$O) δ ppm:

3.25–3.80(4H, m), 4.22(1H, dd, J=6, 8 Hz), 4.48–4.63 (2H, m), 7.41(1H, s), 8.63(1H, s).

(Example 27)

(2R)-N-(2-Nitrooxyethyl)-2-acetylamino-3-nicotinoylthiopropanamide (Exemplary compound No. 28)

The procedures of Example 1 were analogously repeated using 300 mg of (2R)-2-acetylamino-3-nicotinoylthiopropionic acid hydrochloride and 200 mg of 2-nitrooxyethylamine nitrate to give 140 mg of the title compound as colorless columns.

m.p. 110°–112° C.

NMR spectrum (CDCl$_3$) δ ppm:

2.02(3H, s), 3.51(2H, d, J=7 Hz), 3.56–3.64(2H, m), 4.55(2H, t, J=5 Hz), 4.72(1H, dd, J=6, 13 Hz), 6.58(1H, d, J=7 Hz), 7.18(1H, t, J=5 Hz), 7.43(1H, m), 8.20(1H, d, J=7 Hz), 8.81(1H, d, J=6 Hz), 9.16(1H, s).

(Example 28)

(2R)-N-(2-Nitrooxyethyl)-2-acetylamino-3-isobutoxycarbonylthiopanamide (Exemplary compound No. 105)

The procedures of Example 1 were analogously repeated using 0.70 g of (2R)-2-acetylamino-3-isobutoxycarbonylthio)propionic acid and 1.14 g of 2-nitrooxyethylamine nitrate to give 90 mg of the title compound as white crystals.

m.p. 92°–98° C.

NMR spectrum (CDCl$_3$) δ ppm:

0.94(6H, d, J=7 Hz), 1.90–2.10(1H, m), 2.03(3H, s), 3.25(2H, d, J=6 Hz), 3.60(2H, dd, J=5, 11 Hz), 3.97–4.09 (2H, m), 4.54(2H, t, J=5 Hz), 4.63(1H, dd, J=6.13 Hz), 6.60(1H, d, J=7 Hz), 7.08(1H, t, J=5 Hz).

(Example 29)

(2R)-N-(2-Nitrooxyethyl)-2-acetylamino-3-(5-methyl-2-oxo-1,3-dioxolen-4-yl)methoxycarbonylthionamide (Exemplary compound No. 101)

The procedures of Example 1 were analogously repeated using 112 mg of (2R)-2-acetylamino-3-(5-methyl-2-oxo-1,3-dioxolen-4-yl)methoxycarbonylthioproponic acid and 65.2 mg of 2-nitrooxyethylamine nitrate to give 40 mg of the title compound as a colorless oil.

NMR spectrum (CDCl$_3$) δ ppm:

2.07(3H, s), 2.22(3H, s), 3.23–3.39(2H, m), 3.64(2H, dd, J=6, 11 Hz), 4.58(2H, t, J=5 Hz), 4.73(1H, dd, J=7, 13 Hz), 5.01(2H, s), 6.53(1H, d, J=7 Hz), 7.17(1H, t, J=6 Hz).

(Example 30)

(2R)-N-(2-Nitrooxyethyl)-2-amino-3-mercaptopropanamide hydrochloride (Exemplary compound No. 7)

(a) (2R)-N-(2-Nitrooxyethyl)-2-tert-butoxycarbonylamino-3-tert-butoxycarbonylthiopropanamide The procedures of Example 1 were analogously repeated using 322 mg of (2R)-2-tert-butoxycarbonylamino-3-tert-butoxycarbonylthiopropionic acid and 186 mg of 2-nitrooxyethylamine nitrate to give 365 mg of the title compound as a colorless oil.

NMR spectrum (CDCl$_3$) δ ppm:

1.45(9H, s), 1.50(9H, s), 3.16–3.22(2H, m), 3.60–3.65 (2H, m), 4.30–4.32(1H, m), 4.54(2H, t, J=5 Hz), 5.45(1H, d, J=7 Hz), 6.86(1H, bs).

(b) (2R)-N-(2-Nitrooxyethyl)-2-amino-3-mercaptopropanamide hydrochloride

In 1.0 ml of 4N-hydrogen chloride/dioxane were dissolved 365 mg of (2R)-N-(2-nitrooxyethyl)-2-tert-butoxycarbonylamino-3-tert-butoxycarbonylthiopropanamide, and the resulting solution was allowed to stand at room temperature for 1 hour and 35 minutes. To the reaction mixture was added 20 ml of ether, and the precipitates were collected by filtration and dried to give 96 mg of the title compound as a white powder.

NMR spectrum (CDCl$_3$+DMSO-d$_6$) δ ppm:

2.26(1H, t, J=9 Hz), 3.17–3.23(2H, m), 3.45–3.79(2H, m), 4.37(1H, bs), 4.61(2H, m), 8.59(3H, bs), 9.08(1H, bs).

(Reference example 1)

(2R)-2-Acetylamino-3-nicotinoylthiopropionic acid hydrochloride (a) (2R)-2-Acetylamino-3-nicotinoylthiopropionic acid diphenylmethyl ester In 40 ml of anhydrous dichloromethane was suspended 2.0 g of N-acetyl-L-cysteine, and to the suspension were added 5.2 ml of triethylamine and 2.6 g of nicotinoyl chloride hydrochloride with ice-cooling. The mixture was stirred at room temperature for 30 hours. After 20 ml of methanol was added to the reaction mixture, 2.9 g of diphenyldiazomethane were added to the mixture, and the mixture was stirred at room temperature for 40 minutes. After the solvent was evaporated under reduced pressure and the residue was dissolved in ethyl acetate, the solution was washed with aqueous sodium bicarbonate. After the ethyl acetate layer was dried over anhydrous magnesium sulfate, the solvent was evaporated under reduced pressure. The residue was purified by column chromatography through silica gel using hexane-ethyl acetate (1:2) as an eluent to give 0.63 g of the title compound as a pale yellow foam.

NMR spectrum (CDCl$_3$) δ ppm:

2.00(3H, s), 3.54–3.75(2H, m), 5.05(1H, dd, J=5, 13 Hz), 6.32(1H, d, J=7 Hz), 6.98(1H, s), 7.20–7.45(11H, m), 8.09 (1H, d, J=5 Hz), 8.78(1H, d, J=5 Hz), 9.06(1H, s).

(b) (2R)-2-Acetylamino-3-nicotinoylthiopropionic acid hydrochloride

To 0.63 g of (2R)-2-acetylamino-3-nicotinoylthiopropionic acid diphenylmethyl ester obtained in Reference Example 1a were added 10 ml of a solution of 4N-hydrogen chloride/dioxane and 1.0 ml of anisole, and the resulting mixture was stirred at room temperature for 1 hour. The solvent was evaporated under reduced pressure, and to the residue was added water to dissolve it therein, and washed with ethyl acetate. The aqueous layer was evaporated under reduced pressure to give 0.31 g of the title compound as a pale yellow foam.

NMR spectrum (CDCl$_3$+DMSO-d$_6$) δ ppm:

1.85(3H, s), 3.23–3.70(2H, m), 4.45–4.60(1H, m), 4.63 (1H, dd, J=5, 8 Hz), 8.30–8.46(2H, m), 8.89(1H, d, J=5 Hz), 9.09(1H, s).

(Reference example 2)

(2R)-2-Acetylamino-3-(5-methyl-2-oxo-1,3-dioxolen-4-yl) methoxycarbonylthiopropionic acid (a) (2R)-2-Acetylamino-3-(5-methyl-2-oxo-1,3-dioxolen-4-yl)methoxycarbonylthiopropionic acid diphenylmethyl ester In 10 ml of anhydrous dichloromethane were dissolved 182 mg of triphosgene, and to the solution was added a solution of 234 mg of 5-methyl-2-oxo-1,3-dioxolene-4-methanol and 0.15 ml of pyridine in 10 ml of anhydrous dichloromethane. The solution was stirred with ice-cooling for 1 hour and further at room temperature for 30 minutes. To a solution of 500 mg of N-acetyl-L-cysteinediphenylmethyl ester and 0.253 ml of triethylamine in 20 ml of anhydrous dichloromethane was added dropwise the solution obtained above with stirring under ice-cooling. The resulting mixture was stirred at room temperature for 18 hours and further heated with reflux for 4 hours. The solvent was evaporated under reduced pressure, and the residue was dissolved in ethyl acetate and washed with a saturated aqueous sodium chloride. After the resulting mixture was dried over anhydrous magnesium sulfate and the solvent was evaporated under reduced pressure, the residue was purified by column chromatography through silica gel using hexane-ethyl acetate (2:1) as an eluent to give 200 mg of the title compound as a pale yellow material.

NMR spectrum (CDCl$_3$) δ ppm:

2.00(3H, s), 2.14(3H, s), 3.30(1H, dd, J=6, 14 Hz), 3.52(1H, dd, J=5, 14 Hz), 4.85(2H, s), 4.63–5.05(1H, m), 6.25(1H, d, J=5 Hz), 6.87(1H, s), 7.20–7.45(10H, m).

(b) (2R)-2-Acetylamino-3-(5-methyl-2-oxo-1,3-dioxolen-4-yl)methoxycarbonlthioporopionic acid In 1.0 ml of trifluoroacetic acid and several droplets of anisole were dissolved 190 mg of (2R)-2-acetylamino-3-(5-methyl-2-oxo-1,3-dioxolen-4-yl) methoxycarbonylthiopropionic acid diphenylmethyl ester obtained in Reference Example 2a, and the resulting solution was stirred at room temperature for 30 minutes. The solvent was evaporated under reduced pressure, and the residue was washed with hexane to give 120 mg of the title compound as a colorless oil.

NMR spectrum (CDCl$_3$) δ ppm:

2.07(3H, s), 2.19(3H, s), 3.35(1H, dd, J=7, 14 Hz), 3.51(1H, dd, J=5, 14 Hz), 4.75–4.88(1H, m), 4.98(2H, s), 6.58(1H, d, J=7 Hz).

We claim:

1. An amino acid compound of the following formula (I):

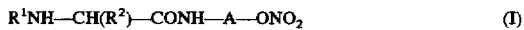

(I)

wherein R$^1$ is hydrogen atom, a C$_1$–C$_5$ alkanoyl group, a C$_1$–C$_4$ alkoxycarbonyl group, a benzyloxycarbonyl group, a furylcarbonyl group, a thienylcarbonyl group, a nicotinoyl group or an isonicotinoyl group;

R$^2$ is a C$_1$–C$_4$ alkyl group having a substituent, said substituent is a mercapto group, a C$_1$–C$_5$ alkanoylthio group, a C$_1$–C$_4$ alkoxycarbonylthio group, a (5-methyl-2-oxo-1,3-dioxolen-4-yl)methoxycarbonylthio group, a C$_6$–C$_{10}$ arylcarbonylthio group or a 5- or 6-membered aromatic heterocyclic carbonylthio group containing 1 nitrogen atom, oxygen atom or sulfur atom; and A is an ethylene group.

2. The compound according to claim 1 wherein R$^1$ is a hydrogen atom, an acetyl, propionyl, butyryl, isobutyryl or pivaloyl group.

3. The compound according to claim 1 wherein R$^2$ is a mercaptomethyl, acetylthiomethyl, isobutyrylthiomethyl, pivaloylthiomethyl, benzoylthiomethyl or ethoxycarbonylthiomethyl group.

4. The compound according to claim 1 wherein R$^1$ is a hydrogen atom, an acetyl, propionyl, butyryl, isobutyryl or pivaloyl group;

R$^2$ is a mercaptomethyl, acetylthiomethyl, isobutyrylthiomethyl, pivaloylthiomethyl, benzoylthiomethyl or ethoxycarbonylthiomethyl group; and A is an ethylene group.

5. N-(2-Nitrooxyethyl)-2-amino-3-mercaptopropanamide and pharmacologically acceptable salts thereof.

6. N-(2-Nitrooxyethyl)-2-acetylamino-3-mercaptopropanamide and pharmacologically acceptable salts thereof.

7. N-(2-Nitrooxyethyl)-2-acetylamino-3-acetylthiopropanamide and pharmacologically acceptable salts thereof.

8. N-(2-Nitrooxyethyl)-2-acetylamino-3-pivaloylthiopropanamide and pharmacologically acceptable salts thereof.

9. N-(2-Nitrooxyethyl)-2-acetylamino-3-ethoxycarbonylthiopropanamide and pharmacologically acceptable salts thereof.

10. N-(2-Nitrooxyethyl)-2-acetylamino-3-benzoylthiopropanamide and pharmacologically acceptable salts thereof.

11. N-(2-Nitrooxyethyl)-2-isobutyrylamino-3-isobutyrylthiopropanamide and pharmacologically acceptable salts thereof.

12. N-(2-Nitrooxyethyl)-2-acetylamino-3-(5-methyl-2-oxo-1,3-dioxolen-4-yl)methoxycarbonylthiopropanamide and pharmacologically acceptable salts thereof.

13. An angina pectoris therapeutic composition comprising an anti-anginal effective amount of a compound according to claim 1 and a pharmacologically acceptable adjuvant.

14. The angina pectoris therapeutic composition according to claim 13 wherein $R^1$ is a hydrogen atom, an acetyl, propionyl, butyryl, isobutyryl or pivaloyl group.

15. The angina pectoris therapeutic composition according to claim 13 wherein $R^2$ is a mercaptomethyl, acetylthiomethyl, isobutyrylthiomethyl, pivaloylthiomethyl, benzoylthiomethyl or ethoxycarbonylthiomethyl group.

16. The angina pectoris therapeutic composition according to claim 13 wherein $R^1$ is a hydrogen atom, an acetyl, propionyl, butyryl, isobutyryl or pivaloyl group;

$R^2$ is a mercaptomethyl, acetylthiomethyl, isobutyrylthiomethyl, pivaloylthiomethyl, benzoylthiomethyl or ethoxycarbonylthiomethyl group.

17. The angina pectoris therapeutic composition according to claim 13 wherein the active ingredient is selected from the following compounds:

N-(2-nitrooxyethyl)-2-amino-3-mercaptopropanamide and pharmacologically acceptable salts thereof;

N-(2-nitrooxyethyl)-2-acetylamino-3-mercaptopropanamide and pharmacologically acceptable salts thereof;

N-(2-nitrooxyethyl)-2-acetylamino-3-acetylthiopropanamide and pharmacologically acceptable salts thereof;

N-(2-nitrooxyethyl)-2-acetylamino-3-pivaloylthiopropanamide and pharmacologically acceptable salts thereof;

N-(2-nitrooxyethyl)-2-acetylamino-3-ethoxycarbonylthiopropanamide and pharmacologically acceptable salts thereof;

N-(2-nitrooxyethyl)-2-acetylamino-3-benzoylthiopropanamide and pharmacologically acceptable salts thereof;

N-(2-nitrooxyethyl)-2-isobutyrylamino-3-isobutyrylthiopropanamide and pharmacologically acceptable salts thereof; and N-(2-nitrooxyethyl)-2-acetylamino-3-(5-methyl-2-oxo-1,3-dioxolen-4-yl)methoxycarbonylthiopropanamide and pharmacologically acceptable salts thereof.

18. A method for treating a patient suffering from angina pectoris comprising administering to the patient an effective anti-anginal amount of the compound of claim 1.

19. The method according to claim 18, wherein the compound is selected from the group consisting of N-(2-nitrooxyethyl)-2-amino-3-mercaptopropanamide, N-(2-nitrooxyethyl)-2-acetylamino-3-mercaptopropanamide, N-(2-nitrooxyethyl)-2-acetylamino-3-acetylthiopropanamide, N-(2-nitrooxyethyl)-2-acetylamino-3-pivaloylthiopropanamide, N-(2-nitrooxyethyl)-2-acetylamino-3-ethoxycarbonylthiopropanamide, N-(2-nitrooxyethyl)-2-acetylamino-3-benzoylthiopropanamide, N-(2-nitrooxyethyl)-2-isobutyrylamino-3-isobutyrylthiopropanamide, N-(2-nitrooxyethyl)-2-acetylamino-3-(5-methyl-2-oxo-1,3-dioxolen-4-yl)methoxycarbonylthiopropanamide and pharmacologically acceptable salts thereof.

* * * * *

UNITED STATES PATENT AND TRADEMARK OFFICE
CERTIFICATE OF CORRECTION

Page 1 of 2

PATENT NO. : 5,705,527
DATED : January 6, 1998
INVENTOR(S) : ISHIHARA et al

It is certified that error appears in the above-identified patent and that said Letters Patent is hereby corrected as shown below:

Title Page, left column, under "Related U.S. Application Data", after "170,174" insert --now abandoned--.

Column 6, line 45: before "N" insert --17:--.
          line 47: before "N" insert --21:--.
          line 49: before "N" insert --23:--.
          line 51: before "N" insert --25:--.
          line 53: before "N" insert --26:--.
          line 55: before "N" insert --47:--.
          line 57: before "N" insert --101:--.

Column 21, line 2 (Claim 5): after "thereof" insert --according to claim 1--.

Column 21, line 5 (Claim 6): after "thereof" insert --according to claim 1--.

Column 21, line 8 (Claim 7): after "thereof" insert --according to claim 1--.

UNITED STATES PATENT AND TRADEMARK OFFICE
CERTIFICATE OF CORRECTION

PATENT NO.   : 5,705,527
DATED        : January 6, 1998
INVENTOR(S)  : ISHIHARA et al It is certified that error appears in the above-identified patent and that said Letters Patent is hereby corrected as shown below:

```
Column 21, line 11 (Claim 8): after "thereof" insert
--according to claim 1--.

Column 21, line 14 (Claim 9): after "thereof" insert
--according to claim 1--.

Column 21, line 17 (Claim 10): after "thereof" insert
--according to claim 1--.

Column 21, line 20 (Claim 11): after "thereof" insert
--according to claim 1--.

Column 21, line 23 (Claim 12): after "thereof" insert
--according to claim 1--.
```

Signed and Sealed this

Sixteenth Day of November, 1999

Q. TODD DICKINSON

Attest:

Attesting Officer

Acting Commissioner of Patents and Trademarks